United States Patent [19]

Dimsdale

[11] 4,261,994

[45] Apr. 14, 1981

[54] 1,2,4-OXADIAZOLE DERIVATIVES, THEIR PREPARATION AND PHARMACEUTICAL USE

[75] Inventor: Michael J. Dimsdale, Villebon sur Yvette, France

[73] Assignee: Synthelabo, Paris, France

[21] Appl. No.: 922,527

[22] Filed: Jul. 7, 1978

[30] Foreign Application Priority Data

Jul. 12, 1977 [FR] France ............................ 77 21447
Jun. 8, 1978 [FR] France ............................ 78 17114

[51] Int. Cl.³ .................. A61K 31/42; A61K 31/495; C07D 271/06; C07D 241/02
[52] U.S. Cl. .................................. 424/250; 542/425; 544/367; 548/133; 424/272
[58] Field of Search .................. 260/307 G; 542/425; 424/272, 250; 548/133; 544/367

[56] References Cited

U.S. PATENT DOCUMENTS

| | | | |
|---|---|---|---|
| 3,452,035 | 6/1969 | Berkelhammer et al. | 260/307 G |
| 3,538,087 | 11/1970 | Troxler et al. | 260/307 G |
| 3,557,099 | 1/1971 | Breuer | 260/307 G |
| 3,564,606 | 2/1971 | Breuer | 260/307 G |
| 3,720,685 | 3/1973 | Breuer et al. | 260/307 G |
| 3,862,168 | 1/1975 | Findeisen et al. | 260/307 G |
| 3,879,407 | 4/1975 | Hagarty | 260/307 G |

FOREIGN PATENT DOCUMENTS

| | | | |
|---|---|---|---|
| 2100924 | 2/1975 | France | 260/307 G |
| 1053825 | 3/1964 | United Kingdom | 548/131 |
| 1053825 | 1/1967 | United Kingdom | 260/307 G |

Primary Examiner—Donald G. Daus
Assistant Examiner—D. B. Springer
Attorney, Agent, or Firm—Wegner & Bretschneider

[57] ABSTRACT

1,2,4-Oxadiazole derivatives of the formula

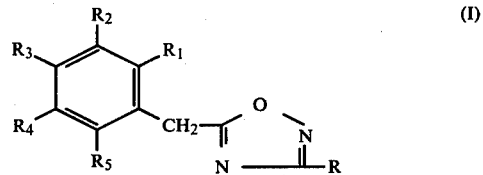

(I)

wherein $R_1$, $R_2$, $R_3$, $R_4$ and $R_5$=H, halogen or alkyl, or two of them represent the —CH=CH—CH=CH— group required to form a fused benzene ring and R=an amino radical NR'R" or —N=CR'₃—NR'₁R'₂, in which R', R", R'₁ and R'₂=alkyl, hydroxyalkyl or N,N-dialkylaminoalkyl or NRR' or NR'₁R'₂=heterocyclic ring, and R' and R" can also be H, dialkylaminoalkylcarbonyl and pyridinoalkyl, (at least two of $R_1$ to $R_5$ being other than H when R' and R"=H), are pharmaceutically useful as anti-hypertensive agents.

6 Claims, No Drawings

1,2,4-OXADIAZOLE DERIVATIVES, THEIR PREPARATION AND PHARMACEUTICAL USE

The compounds of the invention correspond to the formula (I)

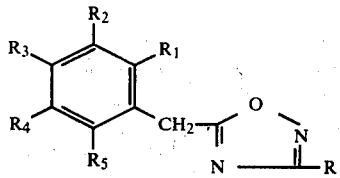
(I)

in which $R_1$, $R_2$, $R_3$, $R_4$ and $R_5$ each represent, independently of one another, a hydrogen or halogen atom or an alkyl radical, or two of the adjacent radicals R together form a bridge —CH=CH—CH=CH—, thus completing a naphthyl radical, two of the radicals $R_1$ to $R_5$ being different from H when R is $NH_2$, and R represents a radical NR'R" in which R' represents a hydrogen atom, a dialkylaminoalkyl radical, a hydroxyalkyl radical, a dialkylaminoalkoxycarbonyl radical, a pyridinoalkyl radical or an alkyl radical and R" represents a hydrogen atom or an alkyl radical, or N, R' and R" together form a heterocyclic ring which can contain another hetero-atom, it being possible for the latter to carry an alkyl, or a radical

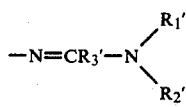

in which $R'_3$ represents a hydrogen atom or an alkyl, aryl or aralkyl radical and $R'_1$ and $R'_2$ independently of one another represent an alkyl radical, a hydroxyalkyl radical or a dialkylaminoalkyl radical, or N, $R'_1$ and $R'_2$ together form a heterocyclic ring which can contain another heteroatom, it being possible for the latter to carry an alkyl substituent, the above alkyl radicals having from 1 to 4 carbon atoms.

Certain compounds of the invention form addition salts with pharmaceutically acceptable acids; these salts form part of the invention. Among pharmaceutically acceptable acid addition salts within the invention are hydrochloride and methanesulphonate salts.

Preferably each of $R_1$, $R_2$, $R_3$, $R_4$ and $R_5$ independently represents a hydrogen atom, a chlorine or fluorine atom or a methyl radical. A special group of compounds is formed by those in which $R_1$ and $R_5$ each represent, independently of one another, a chlorine atom, a fluorine atom or a methyl radical. In this special group of compounds $R_2$, $R_3$ and $R_4$ preferably represent hydrogen atoms.

The alkyl radicals in the groups R are preferably methyl radicals.

It is especially preferred that at least one of R' and R" or at least one of $R'_1$ and $R'_2$ represent methyl radicals. The most preferred R groups are of formula NR'R" or

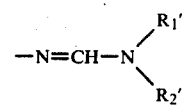

in which R' and R" or $R'_1$ and $R'_2$, respectively represent methyl or 2-hydroxyethyl groups when N, R' and R" or N,$R'_1$ and $R'_2$ together form a heterocyclic ring, the heterocyclic ring can contain another hetero atom, such as nitrogen, which can be substituted by an alkyl radical having from 1 to 4 carbon atoms, preferably methyl. The —NR'R" and —NR'$_1$R'$_2$ groups are desirably 4-methylpiperazin-1-yl groups.

Hydroxyalkyl groups represented by R', R", $R'_1$ and $R'_2$ include 2-hydroxyethyl (—CH$_2$CH$_2$OH) and tris(hydroxymethyl)methyl [—C(CH$_2$OH)$_3$].

According to the invention, the compounds can be prepared by reacting a compound of the formula (II)

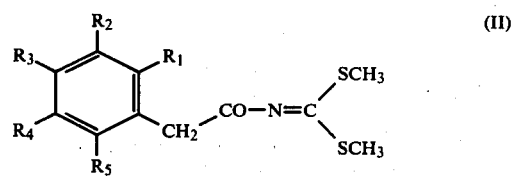
(II)

with ammonia or an amine HNR'R" (III) and then reacting the intermediate obtained with hydroxylamine.

The reaction can be carried out in a solvent such as a lower alcohol, acetone, benzene, an ether or chloroform, but preferably in methanol.

The compounds (I), of the invention, in which R=NH$_2$ can also be prepared by reacting a compound of the formula (V)

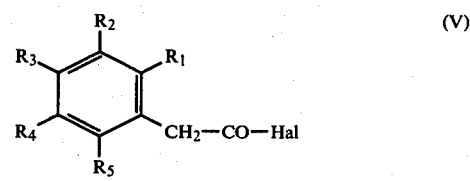
(V)

with cyanamide, NH$_2$CN, and then reacting the intermediate obtained with hydroxylamine.

The first part of the reaction can be carried out at a temperature ranging from 0° to 10° C. in a water/acetone mixture which has been rendered alkaline.

The second part of the reaction can be carried out in a polar solvent such as an alcohol, in the presence of a tertiary base, without isolating the intermediate.

The compounds in which

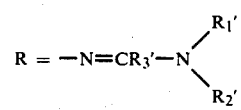

can be prepared from the corresponding compound (I) in which R=NH$_2$, either by reaction with a compound

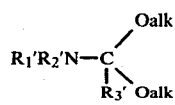

(IV) or by reaction with the compound (alkO)$_3$CR'$_3$ and then with an amine R'$_1$R'$_2$NH. "Alk" represents an alkyl group, conveniently having from 1 to 4 carbon atoms.

The reaction with the compound (IV) can be carried out in a solvent such as an ether, chloroform, a hydrocarbon such as benzene, or a lower alcohol, but preferably in chloroform.

Acid addition salts can be prepared in a manner known in itself, by e.g. reaction of the free base with an acid or by use of acid conditions in the last stage of the preparative reaction, where appropriate. Thus, as shown in Example 4 the hydroxylamine can be employed in the form of its hydrochloride.

The reaction schemes are as follows:

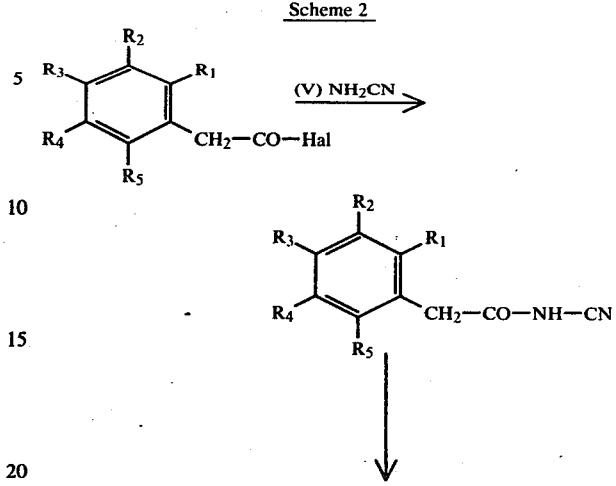

Scheme 2

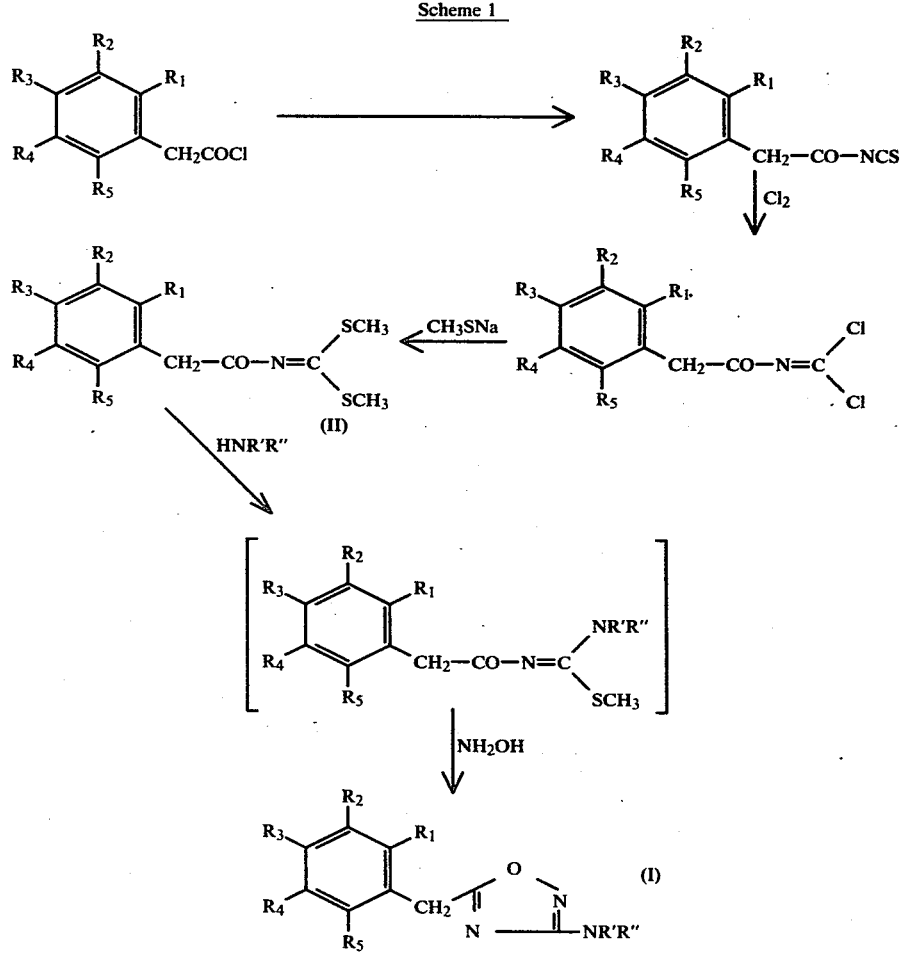

Scheme 1

The compounds (II) are new and form part of the invention.

They are obtained by the method of F. Eloy and A. Van Oventraeten [Chimie Thér., 4, 9 (1969)] from the corresponding acid chloride.

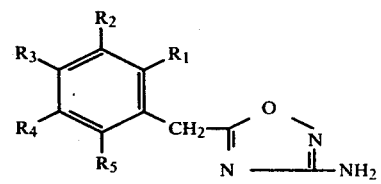

The compounds (V) are known and described in the literature. They can be obtained from the substituted toluene in the conventional manner (via the bromide, the cyanide and the acid).

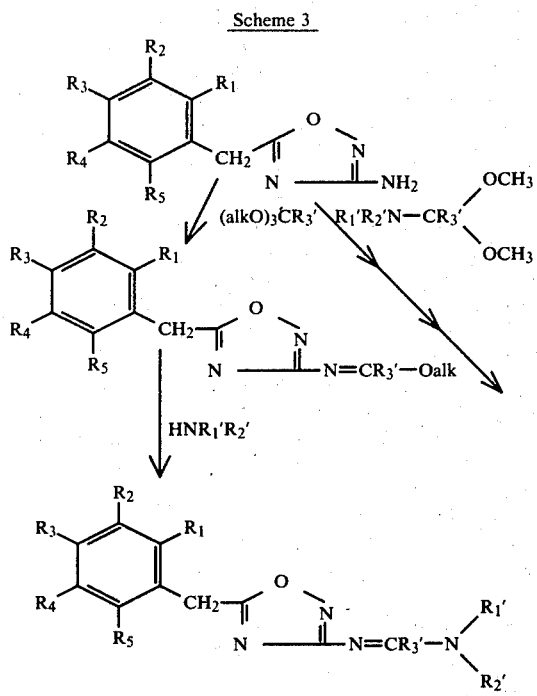

Scheme 3

The following examples illustrate the invention.
The analyses and the IR and NMR spectra confirmed the structure of the compounds.

EXAMPLE 1

3-(4-Methylpiperazin-1-yl)-5-(2,6-dichlorobenzyl)-1,2,4-oxadiazole and its methanesulphonate 1.
N-Dichloromethylene-(2,6-dichlorophenyl)-acetamide 40.26 g (0.18 mol) of (2,6-dichlorophenyl)acetyl chloride and 15 g (0.198 mol) of ammonium thiocyanate are heated for about 10 minutes in 500 ml of acetone. The cooled mixture is filtered, the solid is washed with acetone and the filtrate is evaporated to dryness. Dry ether is added to the oily residue. A yellow crystalline solid is formed and is filtered off. The filtrate is evaporated to dryness. 2,6-Dichlorophenacyl isothiocyanate is obtained in the form of an orange-red oil.

This compound is dissolved in 300 ml of carbon disulphide and a stream of chlorine is passed into the solution under UV irradiation.

The solvent is removed and the residual oil is distilled in vacuo.

The product, which is a pale yellow oil, boils at 122°–4° C./0.15 mm Hg.

2.
N-Bis-(methylthio)-methylene-(2,6-dichlorophenyl)-acetamide

A solution of methanethiol (0.2 mol) in 100 ml of benzene is treated with 8.8 g (0.22 mol) of powdered sodium hydroxide.

A solution in 50 ml of benzene of 26.4 g (0.1 mol) of the compound obtained above is added slowly in the course of about 15 minutes. The mixture is heated under reflux for ¾ hour with continual addition of methanethiol.

The cooled solution is filtered and the filtrate is evaporated to dryness. An oil is obtained which crystallises rapidly. The product is recrystallised from hexane.
Melting point = 86.5°–87° C.

3.
3-(4-Methylpiperazin-1-yl)-5-(2,6-dichlorobenzyl)-1,2,4-oxadiazole, its methanesulphonate and its hydrochloride 6.16 g (0.02 mol) of the preceding product and 2.0 g (0.02 mol) of N-methylpiperazine in 60 ml of methanol are heated at the reflux temperature for 2 hours. 6.96 g (0.1 mol) of hydroxylamine hydrochloride, 19 ml (0.1 mol) of a 5.29 molar solution of sodium methoxide, 50 ml of methanol and 50 ml of water are added to the cooled solution. The mixture is stirred at ambient temperature for one night.

The clear solution is concentrated and the pH is brought to 5 with hydrochloric acid. The crystalline salt is filtered off washed with a small amount of water and dried. The hydrochloride obtained is recrystallised from a mixture of methanol and ether.
Melting point = 273°–5° C. (decomposition).

The free base is obtained from this salt by adding 2 N sodium hydroxide and then extracting with methylene chloride.
Melting point = 121.5°–122.5° C.
The methanesulphonate melts at 193.7° C.

EXAMPLE 2

3-Methylamino-5-(2,6-dichlorobenzyl)-1,2,4-oxadiazole

A solution of 12 cm³ of methylamine in methanol is added to a solution of 6 g (0.019 mol) of N-bis-(methylthio)-methylene-(2,6-dichlorophenyl)-acetamide in 15 cm³ of methanol.

The mixture is stirred for 2 hours. This solution is poured into a solution of 6.75 g (0.097 mol) of hydroxylamine hydrochloride in 19 cm³ of a 5.08 molar solution of sodium methanolate.

The mixture is left for 48 hours at ambient temperature and concentrated to dryness. The solid formed is taken up in CH₂Cl₂. The product is chromatographed on a silica column.
Melting point = 128.9° C.

EXAMPLE 3

3-[N,N-Bis-(2-hydroxyethyl)-formamidino]-5-(2,6-dichlorobenzyl)-1,2,4-oxadiazole and its hydrochloride 1.
3-Ethoxymethyleneamino-5-(2,6-dichlorobenzyl)-1,2,4-oxadiazole 1 g of 3-amino-5-(2,6-dichlorobenzyl)-1,2,4-oxadiazole is heated in air at 150° C. for 3 hours with a few ml of ethyl orthoformate in an amount which is just sufficient to ensure slight agitation. The excess ethyl orthoformate is driven off under reduced pressure. The residue is crystallised from ether.
Melting point = 75° C.

2.

3-[N,N-Bis-(2-hydroxyethyl)-formamidino]-5-(2,6-dichlorobenzyl)-1,2,4-oxadiazole and its hydrochloride 5 g of 3-ethoxymethyleneamino-5-(2,6-dichlorobenzyl)-1,2,4-oxadiazole and 2 g of diethanolamine are dissolved in 70 ml of THF.

After standing for one night, the THF is evaporated off.

The residue is triturated with ether containing 10% of methylene chloride.

The solid obtained is crystallised from a 70/30 mixture of isopropyl ether and isopropanol.

Melting point = 108.8° C.

The monohydrochloride melts at 257° C.

EXAMPLE 4

3-Amino-5-(2,6-dichlorobenzyl)-1,2,4-oxadiazole 4.2 g (0.1 mol) of cyanamide are dissolved in 96 ml of water and 9.6 ml of concentrated sodium hydroxide solution. The solution is cooled to 0°–5° C. in an ice/salt bath and a solution of 23.5 g (0.1 mol) of 2-(2,6-dichlorophenyl)-acetic acid chloride in 50 ml of acetone is added slowly so that the internal temperature of the mixture remains below 5°. The pH of the solution is kept between 10 and 11 by means of a few drops of concentrated sodium hydroxide solution.

When all the acid chloride has been added, the reaction mixture is stirred for 1 hour, whilst checking that the pH and the temperature remain constant.

The mixture is then acidified with 6 N hydrochloric acid at 0°; the intermediate precipitates; it is filtered off or dissolved in chloroform. In the latter case, the solution is washed with water, dried over magnesium sulphate and concentrated to dryness.

The crude intermediate is dissolved in 60 ml of ethanol and the solution obtained is added to a suspension of 10.75 g (0.15 mol) of hydroxylamine hydrochloride in 25 ml of pyridine.

The reaction is slow and very slightly exothermic. The reaction is allowed to proceed for one night. The temperature generally stabilises at about 40°. The precipitated product is filtered off and then washed with ethanol and ether.

The filtrate is concentrated to dryness, the residue is then taken up in water and the solution is rendered alkaline with 2 N sodium hydroxide solution. A second crop of oxadiazole precipitates; it is filtered off and washed with ethanol and ether. The 3-amino-5-(2,6-dichlorobenzyl)-1,2,4-oxadiazole is recrystallised from ethanol and melts at 185° C.

The following Table 1 shows the compounds of the invention which have been prepared, by way of examples, in accordance with one of the methods described above.

HCl = hydrochloride
MeSO₃H = methanesulphonate

TABLE I

| Compound no. | $R_1$ | $R_2$ | $R_3$ | $R_4$ | $R_5$ | R | Melting point (°C.) |
|---|---|---|---|---|---|---|---|
| 1 | Cl | H | H | H | Cl | N(CH₃)₂ | 110.3 |
| 2 (Example 2) | Cl | H | H | H | Cl | NHCH₃ | 128.9 |
| 3 | Cl | H | H | H | Cl | 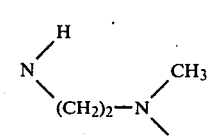 | 193 |
| 4 (Example 1) | Cl | H | H | H | Cl | 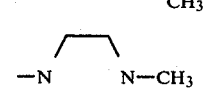 | 121.5–122.5<br>HCl = 273.5–5<br>MeSO₃H = 193.7 |
| 5 | Cl | H | H | H | Cl | 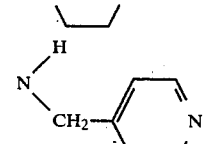 | 114.5–116.5<br>HCl = 206–7 |
| 6 | Cl | H | H | H | Cl | 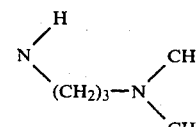 | HCl = 173.5–175 |
| 7 | Cl | H | H | H | Cl | 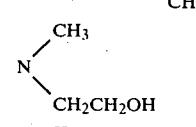 | 72–74 |
| 8 | Cl | H | H | H | Cl | 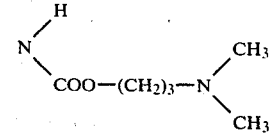 | HCl = 190.3 |

TABLE I-continued

| Compound no. | $R_1$ | $R_2$ | $R_3$ | $R_4$ | $R_5$ | R | Melting point (°C.) |
|---|---|---|---|---|---|---|---|
| 9 | Cl | H | H | H | Cl | N=CH—N(CH$_3$)$_2$ | 138.5–139.5 HCl = 208–12 |
| 10 | Cl | H | H | H | Cl | N=CH—N(piperazine)—N—CH$_3$ | 113 HCl = 257 |
| 11 (Example 3) | Cl | H | H | H | Cl | N=CH—N(CH$_2$CH$_2$OH)$_2$ | 108.8 |
| 12 | Cl | H | H | H | Cl | N=CH—N(CH$_3$)(CH$_2$CH$_2$N(CH$_3$)$_2$) | 103.5 HCl = 220 |
| 13 | Cl | H | H | H | Cl | N=CH—N(CH$_2$—CH$_3$)(C(CH$_2$OH)$_3$) | 144.6 |
| 14 | CH$_3$ | H | H | H | CH$_3$ | N=CH—N(CH$_3$)$_2$ | 89.1 |
| 15 | Cl | H | H | H | F | N=CH—N(CH$_3$)$_2$ | 91 |
| 16 | F | H | H | H | F | NH$_2$ | 169 |
| 17 | F | H | H | H | F | N=CH—N(CH$_3$)$_2$ | 75.2 |
| 18 (Example 4) | Cl | H | H | H | Cl | NH$_2$ | 185 |
| 19 | Cl | H | H | Cl | H | NH$_2$ | 153–5 |
| 20 | H | Cl | Cl | H | H | NH$_2$ | 113–113.5 |
| 21 | Cl | H | Cl | H | H | NH$_2$ | 177 |
| 22 | CH$_3$ | H | H | —CH=CH—CH=CH— | NH$_2$ | | 210–212 |
| 23 | Cl | H | H | H | F | NH$_2$ | 170 |

The compounds of the invention were subjected to pharmacological tests which showed their activity as antihypertensive agents.

The toxicity of the compounds (I) was determined by intraperitoneal administration to CD1 (Charles River) male rats weighing 100 to 120 g, which had fasted for 18 hours.

The 50% lethal dose (LD 50) is indicated in Table II.

The anti-hypertensive activity is evaluated on spontaneously hypertonic male rats in accordance with the method of Gerold and Tschirky (Arzneim. Forsch, 1968, 18, 1,285). The systolic pressure is measured by taking the pulse at the level of the caudal artery.

At a dose of 10 mg/kg (5 mg/day administered orally 2 days in succession), decreases in blood pressure are observed and they are determined after 4 and 24 hours.

The results obtained for certain representative compounds of the invention are indicated in Table II.

TABLE II

| Compound | LD 50 (mg/kg) administered intraperitoneally to rats | Anti-hypertensive activity % | | |
|---|---|---|---|---|
| | | dose(mg/kg) administered orally | 4 hours | 24 hours |
| 1 | — | 20 | −33 | −14 |
| 2 | — | 20 | −18 | −9 |
| 6 | <250 | 20 | −5 | −7 |
| 9 | >500 | 20 | −29 | −15 |
| 10 | <500 | 20 | −29 | |
| 11 | ≧500 | 20 | −32 | |
| 14 | | 20 | −22 | −13 |
| 15 | ≦500 | 5 | −26 | −6 |
| 16 | | 5 | −18 | −1 |
| 18 | 250 | 5 | −18 | −3 |
| 19 | ≧500 | 5 | −18 | −3 |

It should be noted that, in the actimetry test on mice, the sedative action of the compounds of the invention was shown to be negligible.

The results of the pharmacological tests show that the compounds of the invention can be used as medicaments in human and veterinary therapy and as antihypertensive agents in the cardiovascular field.

They are used particularly in the treatment of all forms of genuine or secondary hypertension.

Consequently, the invention embraces all pharmaceutical compositions which contain at least one of the compounds (I) as the active principal, in association with any excipient which is suitable for its administration, which is mainly oral administration but also endorectal or parenteral administration.

The daily posology for oral administration can vary from 4 to 100 mg.

I clam:

1. A compound of the formula:

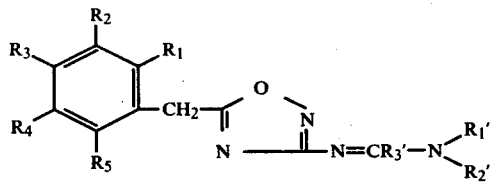

wherein each of $R_1$, $R_2$, $R_3$, $R_4$ and $R_5$ is independently hydrogen, halogen, or $C_{1-4}$alkyl, or two of $R_1$, $R_2$, $R_3$, $R_4$ and $R_5$ bonded to adjacent carbon atoms of the benzene ring form the group —CH=CH—CH=CH, $R'_3$ is hydrogen or $C_{1-4}$alkyl each of $R'_1$ and $R'_2$ independently is $C_{1-4}$ alkyl, hydroxy-($C_{1-4}$alkyl), or N,N-di($C_{1-4}$alkyl)-amino-($C_{1-4}$alkyl), or N, $R'_1$ and $R'_2$ together form methylpiperazino; or a pharmaceutically acceptable acid addition salt thereof.

2. A compound of claim 1, wherein said compound is 3-[N,N-dimethylformamidino]-5-(2,6-dichlorobenzyl)-1,2,4-oxadiazole or a pharmaceutically acceptable acid addition salt thereof.

3. A compound of claim 1, wherein said compound is 3-[N,N-bis(2-hydroxyethyl)-formamidino]-5-(2,6-dichlorobenzyl)-1,2,4-oxadiazole or a pharmaceutically acceptable acid addition salt thereof.

4. A compound of claim 1 wherein said compound is 3-[N,N-dimethylformamidino]-5-(2-chloro-6-fluorobenzyl)-1,2,4-oxadiazole or a pharmaceutically acceptable acid addition salt thereof.

5. A pharmaceutical composition suitable for treating hypertension comprising a compound according to claim 1 in association with a pharmaceutically acceptable excipient, said compound being present in an amount effective to treat hypertension.

6. A method of treating a hypertensive patient to relieve hypertension which comprises administering to said patient a compound of claim 1 in an amount sufficient to relieve hypertension.

* * * * *